(12) United States Patent
Goorevich et al.

(10) Patent No.: US 12,022,262 B2
(45) Date of Patent: *Jun. 25, 2024

(54) FEATURE EXTRACTION IN HEARING PROSTHESES

(71) Applicant: Cochlear Limited, Macquarie University (AU)

(72) Inventors: Michael Goorevich, Naremburn (AU); Matthew Brown, South Coogee (AU); Andrew Vandali, Greenvale (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,024

(22) Filed: Feb. 27, 2023

(65) Prior Publication Data

US 2023/0283971 A1 Sep. 7, 2023

Related U.S. Application Data

(63) Continuation of application No. 16/770,178, filed as application No. PCT/IB2018/059520 on Nov. 30, 2018, now Pat. No. 11,632,634.

(60) Provisional application No. 62/596,170, filed on Dec. 8, 2017.

(51) Int. Cl.
*H04R 25/00* (2006.01)
*A61N 1/36* (2006.01)

(52) U.S. Cl.
CPC ....... *H04R 25/505* (2013.01); *A61N 1/36038* (2017.08); *H04R 2225/41* (2013.01); *H04R 2225/43* (2013.01); *H04R 2225/67* (2013.01)

(58) Field of Classification Search
CPC .... H04R 25/30; H04R 25/505; H04R 25/558; H04R 2225/41; H04R 2460/07
USPC ...................................................... 381/312
See application file for complete search history.

(56) References Cited

U.S. PATENT DOCUMENTS

| 7,231,257 B2 | 6/2007 | McDermott |
| 9,084,893 B2 | 7/2015 | Vandali |
| 9,240,193 B2 | 1/2016 | James |
| 2002/0191799 A1 | 12/2002 | Nordqvist |

(Continued)

FOREIGN PATENT DOCUMENTS

KR 101600426 B1 3/2016

OTHER PUBLICATIONS

International Search Report and Written Opinion received in application No. PCT/IB2018/059520, dated Apr. 1, 2019 (13 pages).

(Continued)

*Primary Examiner* — Sean H Nguyen
(74) *Attorney, Agent, or Firm* — Edell, Shapiro & Finnan, LLC

(57) ABSTRACT

Presented herein are techniques for extracting features from sound signals received at a hearing prosthesis at least partially based on an environmental classification of the sound signals. More specifically, one or more sound signals are received at a hearing prosthesis and are converted in to stimulation control signals for use in delivering stimulation to a recipient of the hearing prosthesis. The hearing prosthesis determines an environmental classification of the sound environment associated with the one or more sound signals and is configured to use the environmental classification in the determination of a feature-based adjustment for incorporation into the stimulation control signals.

22 Claims, 14 Drawing Sheets

(56) References Cited

U.S. PATENT DOCUMENTS

| | | |
|---|---|---|
| 2005/0129262 A1 | 6/2005 | Dillon |
| 2006/0126872 A1 | 6/2006 | Allegro-Baumann et al. |
| 2014/0105433 A1 | 4/2014 | Goorevich et al. |
| 2016/0205481 A1 | 7/2016 | Swanson |
| 2016/0241971 A1 | 8/2016 | Goorevich |
| 2017/0171674 A1 | 6/2017 | Fung et al. |
| 2017/0359659 A1 | 12/2017 | Von Brasch et al. |

OTHER PUBLICATIONS

Vandali et al., "Enhancement of temporal cues to pitch in cochlear implants: Effects on pitch ranking", The Journal of the Acoustical Society of America, Jul. 2012 (12 pages).

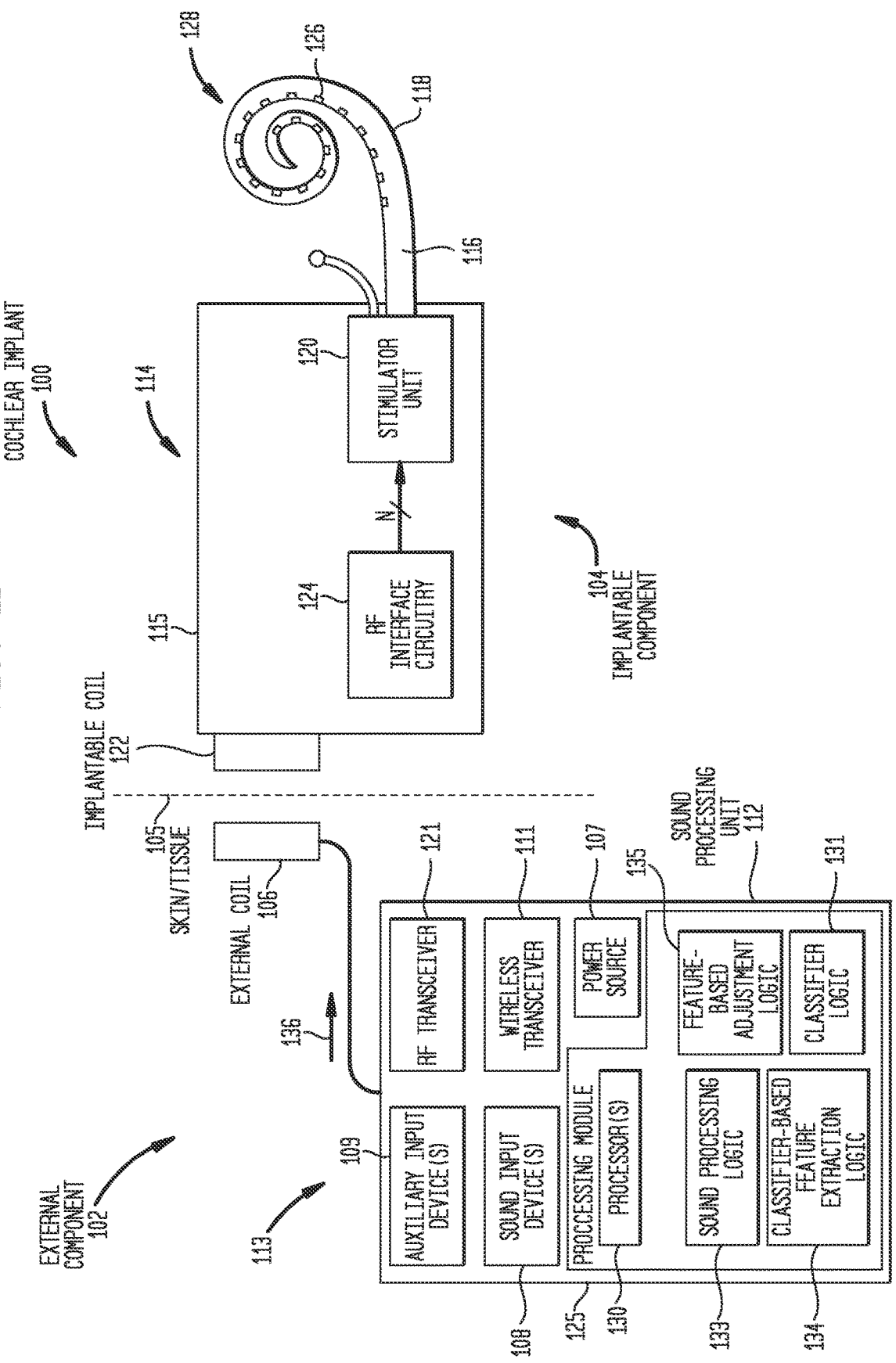

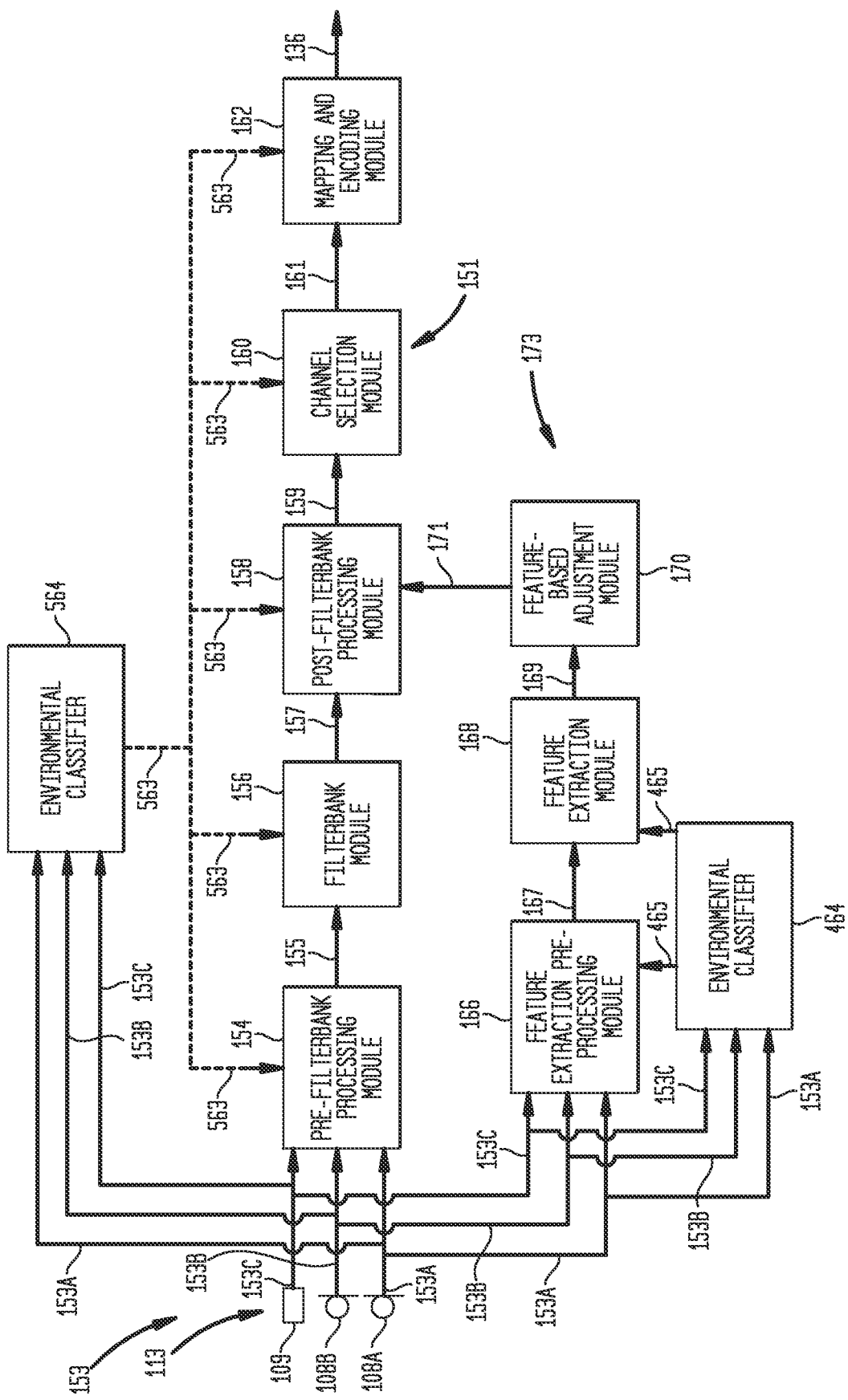

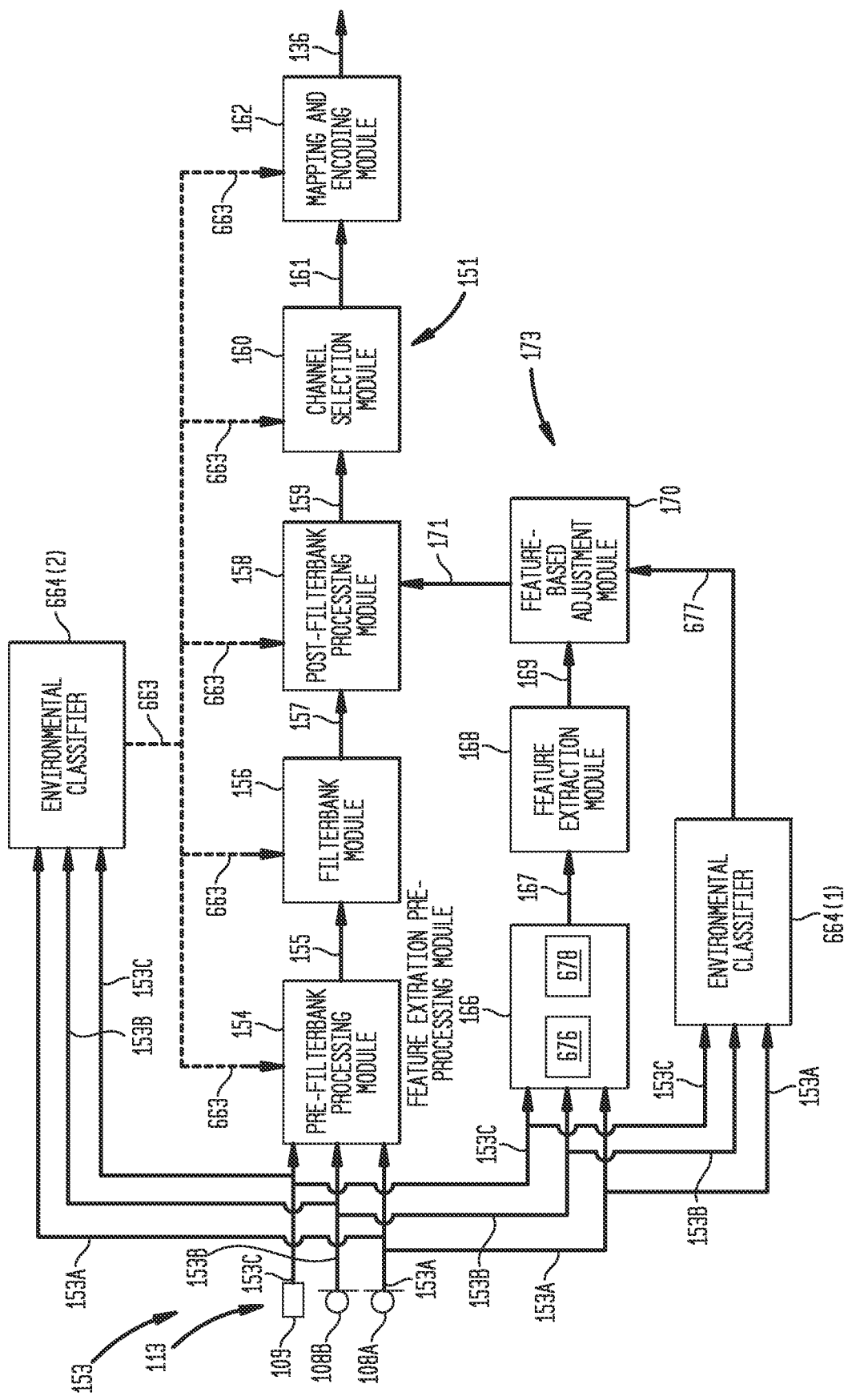

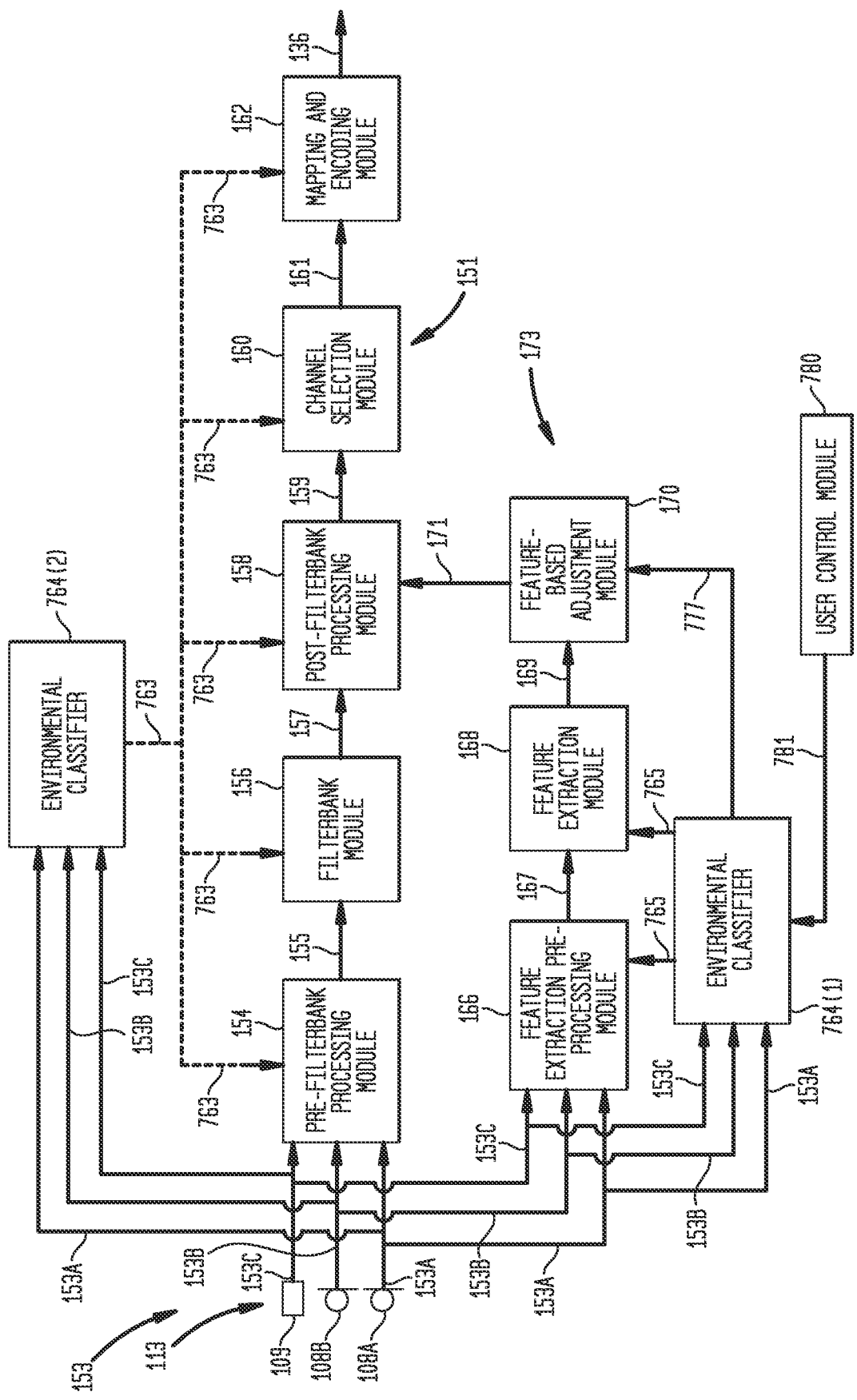

RECEIVING ONE OR MORE SOUND SIGNALS AT A HEARING PROSTHESIS — 1091

DETERMINING, FROM THE ONE OR MORE SOUND SIGNALS, AN ENVIRONMENTAL CLASSIFICATION OF A CURRENT SOUND ENVIRONMENT ASSOCIATED WITH THE ONE OR MORE SOUND SIGNALS — 1092

PERFORMING ONE OR MORE FEATURE-EXTRACTION OPERATIONS TO EXTRACT AT LEAST ONE SIGNAL FEATURE FROM THE ONE OR MORE SOUND SIGNALS, WHEREIN THE ONE OR MORE FEATURE-EXTRACTION OPERATIONS ARE CONTROLLED AT LEAST PARTIALLY BASED ON THE ENVIRONMENTAL CLASSIFFICATION OF THE CURRENT SOUND ENVIRONMENT — 1093

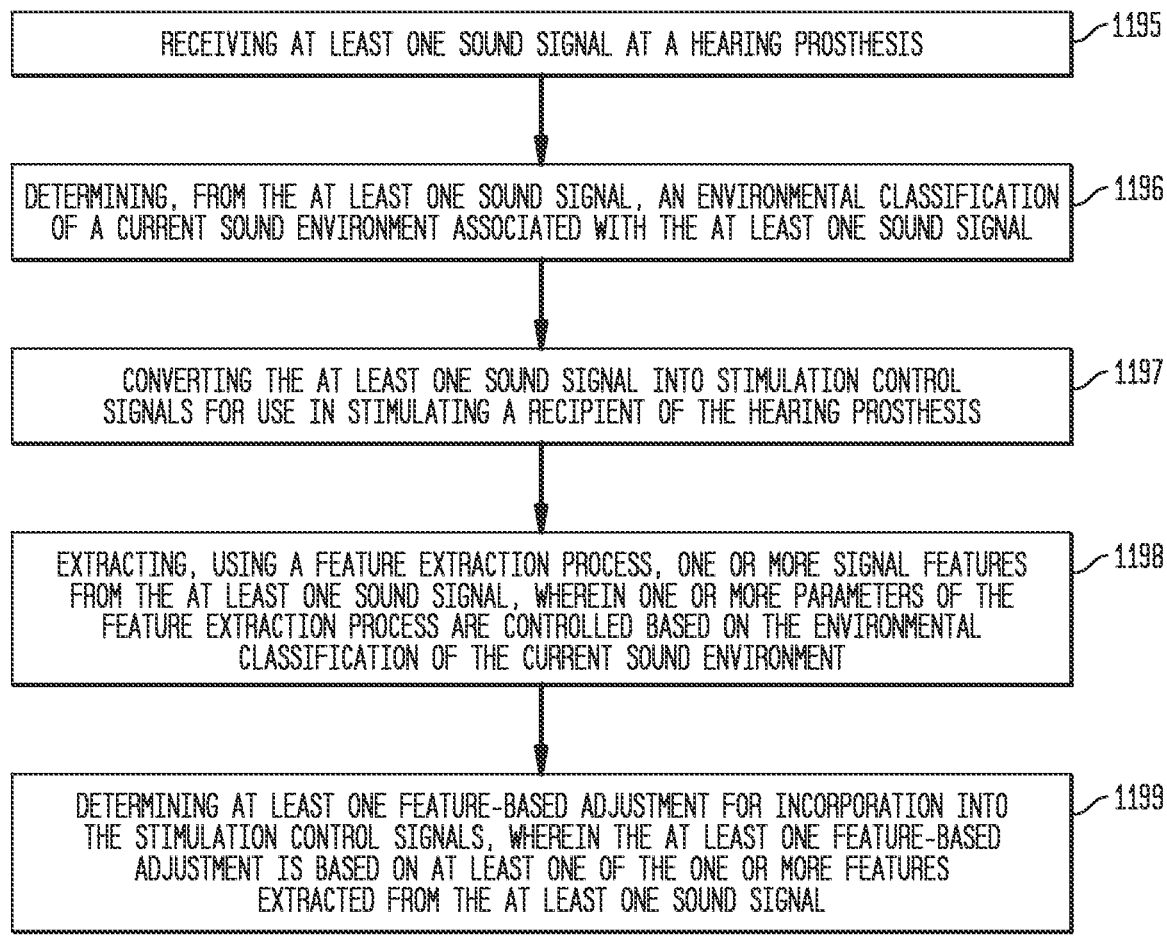

FEATURE EXTRACTION IN HEARING PROSTHESES

BACKGROUND

Field of the Invention

The present invention relates generally to feature extraction in hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: receiving one or more sound signals at a hearing prosthesis; determining, from the one or more sound signals, an environmental classification of a current sound environment associated with the one or more sound signals; and performing one or more feature-extraction operations to extract at least one signal feature from the one or more sound signals, wherein the one or more feature-extraction operations are controlled at least partially based on the environmental classification of the current sound environment.

In another aspect, a method is provided. The method comprises: receiving at least one sound signal at a hearing prosthesis; determining, from the at least one sound signal, an environmental classification of a current sound environment associated with the at least one sound signal; converting the at least one sound signal into stimulation control signals for use in stimulating a recipient of the hearing prosthesis; extracting, using a feature extraction process, one or more signal features from the at least one sound signal, wherein one or more parameters of the feature extraction process are controlled based on the environmental classification of the current sound environment; and determining at least one feature-based adjustment for incorporation into the stimulation control signals, wherein the at least one feature-based adjustment is based on at least one of the one or more features extracted from the at least one sound signal.

In another aspect, a hearing prosthesis is provided. The hearing prosthesis comprises: one or more input devices configured to receive one or more sound signals; and one or more processors coupled to the one or more input devices, the one or more processors configured to: convert the one or more sound signals into one or more stimulation control signals for use in delivering stimulation to a recipient of the hearing prosthesis, determine, from the one or more sound signals, an environmental classification of a current sound environment associated with the one or more sound signals, and extract, using one or more feature extraction operations, one or more features from the one or more sound signals, wherein one or more parameters of the one or more feature extraction operations are controlled based on the environmental classification of the current sound environment.

In another aspect, a hearing prosthesis is provided. The hearing prosthesis comprises: means for receiving one or more sound signals at a hearing prosthesis; means for determining, from the one or more sound signals, an environmental classification of a current sound environment associated with the one or more sound signals; and means for performing one or more feature-extraction operations to extract at least one signal feature from the one or more sound signals, wherein one or more parameters of the one or more feature-extraction operations are at least partially controlled based on the environmental classification of the current sound environment.

BRIEF DESCRIPTION OF THE DRAWINGS

Embodiments of the present invention are described herein in conjunction with the accompanying drawings, in which:

FIG. 1B is a block diagram of the cochlear implant of FIG. 1A;

FIG. 5 is a functional block diagram illustrating further details of a hearing prosthesis configured to implement certain techniques presented herein;

FIG. 6B is a functional block diagram illustrating further details of a hearing prosthesis configured to implement certain techniques presented herein;

FIG. 7 is a functional block diagram illustrating further details of a hearing prosthesis configured to implement certain techniques presented herein;

FIG. 10 is a flowchart of a method, in accordance with certain embodiments presented herein;

FIG. 11 is another flowchart of a method, in accordance with certain embodiments presented herein.

DETAILED DESCRIPTION

Presented herein are techniques for extracting features from sound signals received at a hearing prosthesis at least partially based on an environmental classification of the sound signals. More specifically, one or more sound signals are received at a hearing prosthesis and are converted in to stimulation control signals for use in delivering stimulation to a recipient of the hearing prosthesis. The hearing prosthesis determines an environmental classification of the sound environment (i.e., determines the "class" or "category" of the sound environment) associated with the one or more sound signals and is configured to use the environmental classification in the determination of a feature-based adjustment for incorporation into the stimulation control signals. In certain embodiments, the hearing prosthesis is configured to perform a feature extraction process to extract at least one feature from the one or more sound signals for use in the feature-based adjustment. One or more parameters of the feature extraction process are controlled/adjusted based on the environmental classification of the current sound environment.

There are a number of different types of hearing prostheses in which embodiments of the present invention may be implemented. However, merely for ease of illustration, the techniques presented herein are primarily described with reference to one type of hearing prosthesis, namely a cochlear implant. It is to be appreciated that the techniques presented herein may be used in other hearing prostheses, such as auditory brainstem stimulators, hearing aids, electro-acoustic hearing prostheses, bimodal hearing prosthesis, bilateral hearing prosthesis, etc.

Figure 1A:
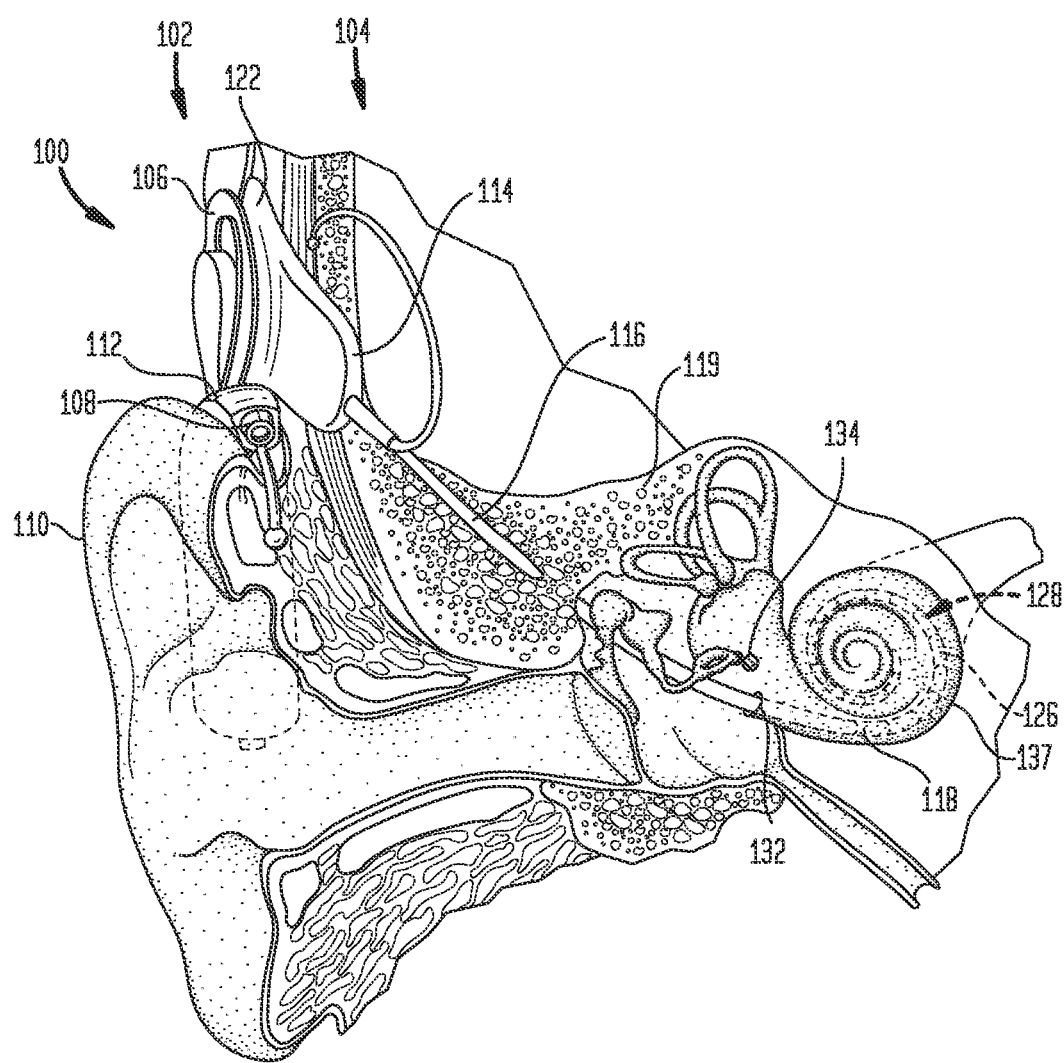
FIG. 1A is a schematic diagram illustrating a cochlear implant, in accordance with certain embodiments presented herein.

FIG. 1A is a schematic diagram of an exemplary cochlear implant 100 configured to implement embodiments of the present invention, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements/devices 113 for receiving sound signals at a sound processing unit 112. In this example, the one or more one or more input devices 113 include sound input devices 108 (e.g., microphones positioned by auricle 110 of the recipient, telecoils, etc.), one or more auxiliary input devices 109 (e.g., audio ports, such as a Direct Audio Input (DAI), data ports, such as a Universal Serial Bus (USB) port, cable port, etc.), and a wireless transmitter/receiver (transceiver) 111, each located in, on, or near the sound processing unit 112.

The sound processing unit 112 also includes, for example, at least one battery 107, a radio-frequency (RF) transceiver 121, and a processing module 125. The processing module 125 comprises one or more processors 130 (e.g., one or more Digital Signal Processors (DSPs), one or more or uC core, etc.) and a number of logic elements (e.g., firmware), including environment classifier logic (classifier logic) 131, sound processing logic 133, classifier-based feature extraction logic 134, and feature-based adjustment logic 135.

FIG. 1B illustrates a simplified firmware implementation for the processing module 125. It is to be appreciated that one or more operations associated with the processing module 125 may be partially or fully implemented with digital logic gates in one or more application-specific integrated circuits (ASICs), partially or fully in software, etc.

In the examples of FIGS. 1A and 1B, the sound processing unit 112 is a behind-the-ear (BTE) sound processing unit configured to be attached to, and worn adjacent to, the recipient's ear. However, it is to be appreciated that embodiments of the present invention may be implemented by sound processing units having other arrangements, such as by a button sound processing unit (i.e., a component having a generally cylindrical shape and which is configured to be magnetically coupled to the recipient's head), etc., a mini or micro-BTE unit, an in-the-canal unit that is configured to be located in the recipient's ear canal, a body-worn sound processing unit, etc.

Returning to the example embodiment of FIGS. 1A and 1B, the implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. The implant body 114 also includes an internal/implantable coil 122 that is generally external to the housing 115, but which is connected to the RF interface circuitry 124 via a hermetic feedthrough (not shown in FIG. 1B).

As noted, stimulating assembly 118 is configured to be at least partially implanted in the recipient's cochlea 137. Stimulating assembly 118 includes a plurality of longitudinally spaced intra-cochlear electrical stimulating contacts (electrodes) 126 that collectively form a contact or electrode array 128 for delivery of electrical stimulation (current) to the recipient's cochlea. Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically couple the electrodes 126 to the stimulator unit 120.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

As noted above, sound processing unit 112 includes the processing module 125. The processing module 125 is configured to convert received sound signals into stimulation control signals 136 for use in stimulating a first ear of a recipient (i.e., the processing module 125 is configured to perform sound processing on sound signals received at the sound processing unit 112). Stated differently, the one or more processors 130 are configured to execute sound processing logic 133 (e.g., firmware) to convert the received sounds signals into stimulation control signals 136 that represent electrical stimulation for delivery to the recipient. The sound signals that are processed and converted into stimulation control signals may be signals received via the sound input devices 108, signals received via the auxiliary input devices 109, and/or signals received via the wireless transceiver 111.

In the embodiment of FIG. 1B, the stimulation control signals 136 are provided to the RF transceiver 121, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate electrical stimulation signals (e.g., current signals) for delivery to the recipient's cochlea via one or more stimulating contacts 126. In this way, cochlear implant 100 electrically stimulates the recipient's auditory nerve cells, bypassing absent or defective hair cells that normally transduce acoustic vibrations into neural activity, in a manner that causes the recipient to perceive one or more components of the received sound signals.

As noted, the processing module 125 in sound processing unit 112 is configured to execute sound processing operations to convert the received sound signals into stimulation control signals 136 (i.e., processed sound signals). In addition to these sound processing operations, as described further below, the processing module 125 is configured to determine an environmental classification of the sound environment (i.e., determines the "class" or "category" of the sound environment) associated with the sound signals. Also as described further below, the processing module 125 is configured to extract at least one signal feature ("feature") from the received sound signals and, based on the at least one least one signal feature, determine at least one feature-based adjustment for incorporation into the stimulation control signals 136. The at least one feature-based adjustment is controlled at least partially based on the signal feature extracted from the sound signals. For example, in certain embodiments, one or more parameters of the feature extraction operations are controlled at least partially based on the environmental classification of the current sound environment.

Figure 2:
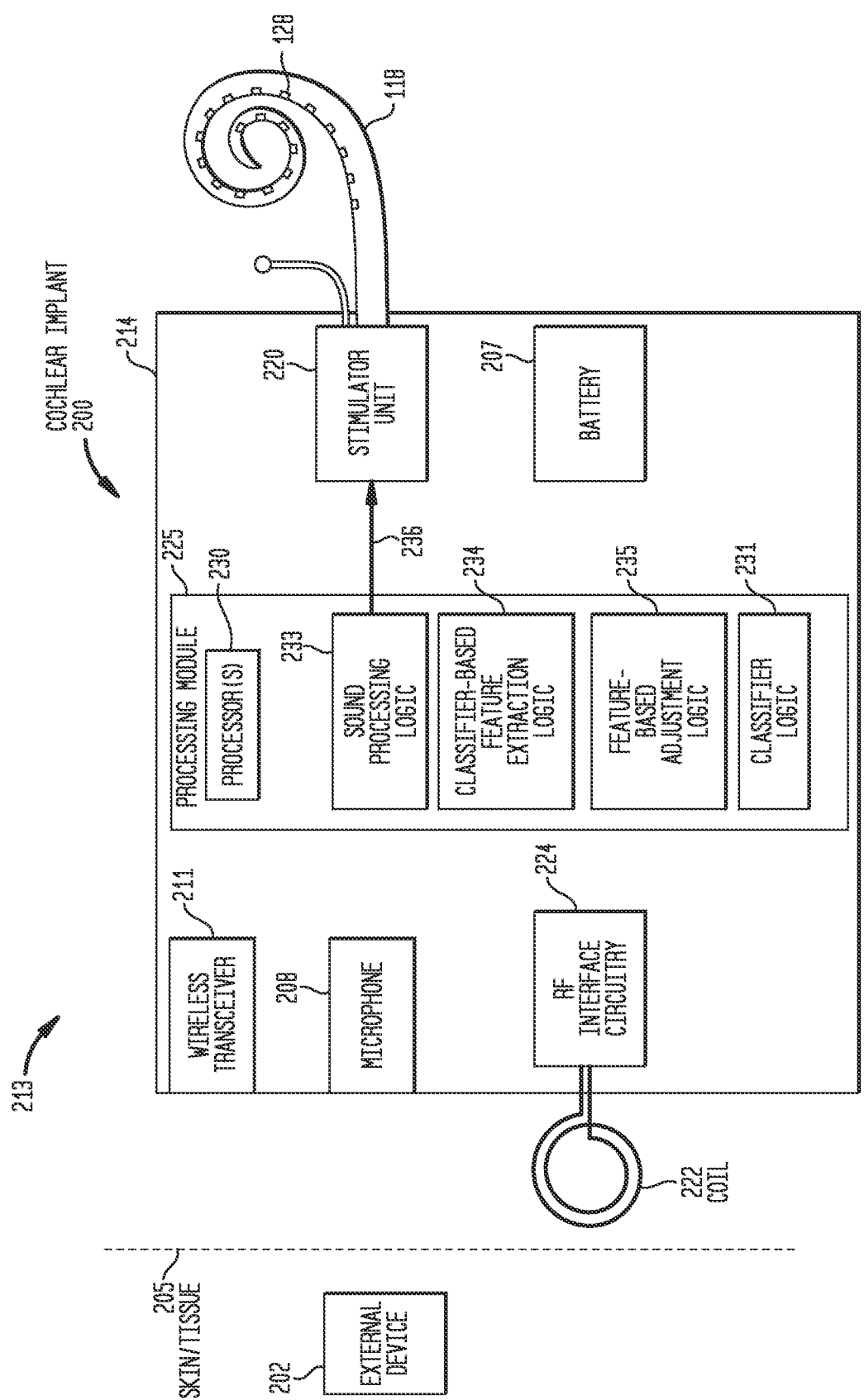
FIG. 2 is a block diagram of a totally implantable cochlear implant, in accordance with certain embodiments presented herein.

FIGS. 1A and 1B illustrate an arrangement in which the cochlear implant 100 includes an external component. However, it is to be appreciated that embodiments of the present invention may be implemented in cochlear implants having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge an internal power source (battery) 207. External device 202 may be a dedicated charger or a conventional cochlear implant sound processor.

Cochlear implant 200 includes an implant body (main implantable component) 214, one or more input elements 213 for receiving sound signals (e.g., one or more implantable microphones 208 and a wireless transceiver 211), an implantable coil 222, and an elongate intra-cochlear stimulating assembly 118 as described above with reference to FIGS. 1A and 1B. The microphone 208 and/or the implantable coil 222 may be positioned in, or electrically connected to, the implant body 214. The implant body 214 further comprises the battery 207, RF interface circuitry 224, a processing module 225, and a stimulator unit 220 (which is similar to stimulator unit 120 of FIGS. 1A and 1B). The processing module 225 may be similar to processing module 125 of FIGS. 1A and 1B, and includes one or more processors 230 and a number of logic elements (e.g., firmware), including environment classifier logic (classifier logic) 231, sound processing logic 233, classifier-based feature extraction logic 234, and feature-based adjustment logic 235, which are similar to the classifier logic 131, sound processing logic 133, the classifier-based feature extraction logic 134, and the feature-based adjustment logic 135, respectively, described elsewhere herein.

In the embodiment of FIG. 2, the one or more implantable microphones 208 are configured to receive sound signals. The processing module 225 is configured to convert received signals into stimulation control signals 236 for use in stimulating a first ear of a recipient. Stated differently, the one or more processors 230 are configured to execute sound processing logic 233 to convert the received sound signals into stimulation control signals 236 that represent electrical stimulation for delivery to the recipient.

As noted above, FIGS. 1A and 1B illustrate an embodiment in which the external component 102 includes the processing module 125. As such, in the illustrative arrangement of FIGS. 1A and 1B, the stimulation control signals 136 are provided to the implanted stimulator unit 120 via the RF link between the external coil 106 and the internal coil 122. However, in the embodiment of FIG. 2 the processing module 225 is implanted in the recipient. As such, in the embodiments of FIG. 2, the stimulation control signals 236 do not traverse the RF link, but instead are provided directly to the stimulator unit 220. The stimulator unit 220 is configured to utilize the stimulation control signals 236 to generate electrical stimulation signals that are delivered to the recipient's cochlea via one or more stimulation channels.

In addition to the sound processing operations, as described further below, the processing module 225 is configured to determine an environmental classification of the sound environment associated with the received sound signals. Also as described further below, the processing module 225 is configured to extract at least one signal feature ("feature") from the received sound signals and, based on the at least one least one signal feature, determine at least one feature-based adjustment for incorporation into the stimulation control signals 236. The at least one feature-based adjustment is controlled at least partially based on the signal feature extracted from the sound signals. For example, in certain embodiments, one or more parameters of the feature extraction operations are controlled at least partially based on the environmental classification of the current sound environment.

As noted, the techniques presented herein may be implemented in a number of different types of hearing prostheses. However, for ease of description, further details of the techniques presented herein will generally be described with reference to cochlear implant 100 of FIGS. 1A-1B.

Figure 3:
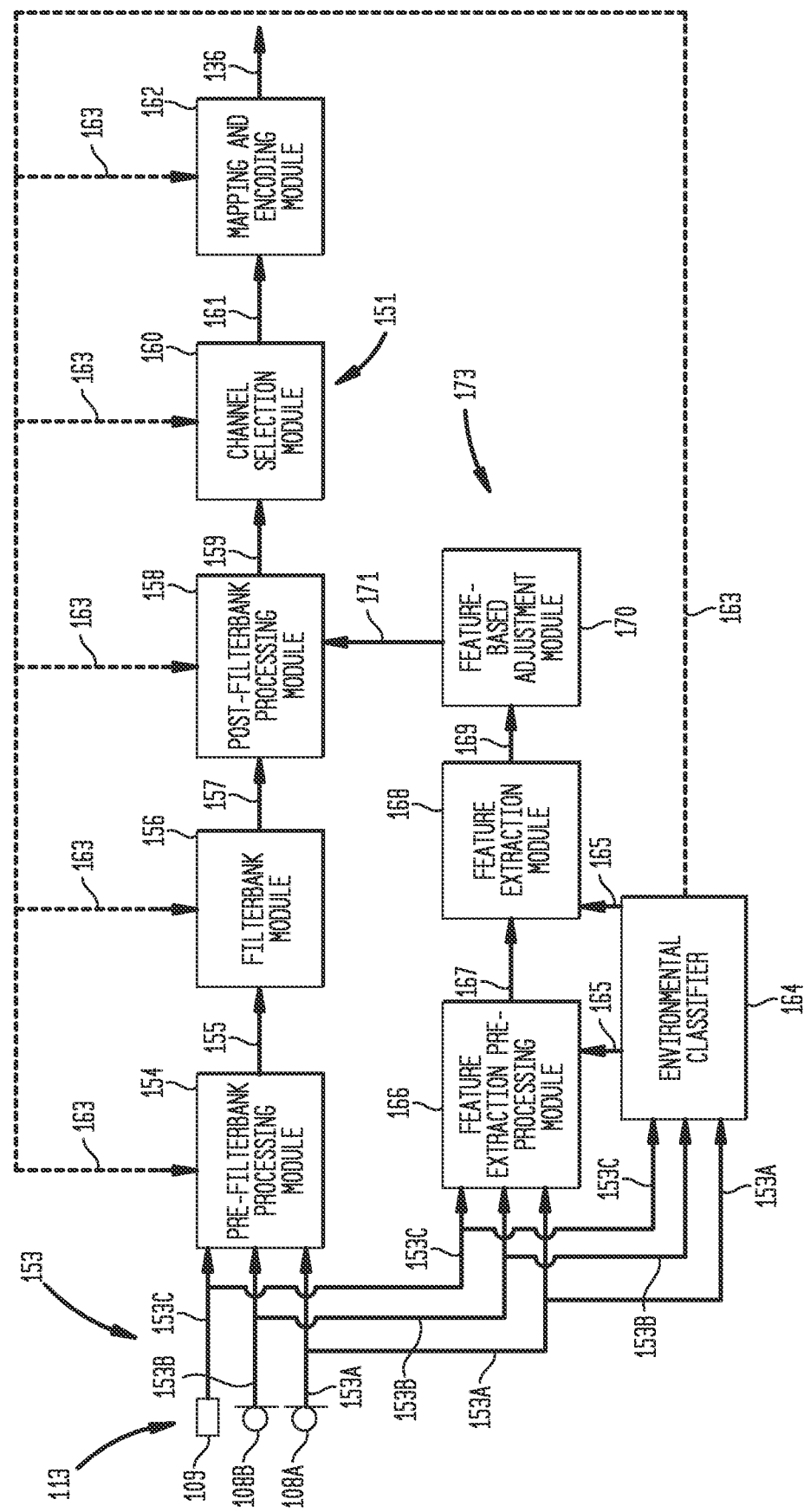
FIG. 3 is a functional block diagram illustrating further details of a hearing prosthesis configured to implement certain techniques presented herein.

More specifically, FIG. 3 is a functional block diagram illustrating further details of the sound processing unit 112 of cochlear implant 100. For ease of illustration, elements that are not related to the sound processing or the classifier-based feature extraction techniques have been omitted from FIG. 3.

As noted, the cochlear implant 100 comprises one or more input devices 113. In the example of FIG. 3, the input devices 113 comprise two sound input devices, namely a first microphone 108A and a second microphone 108B, as well as at least one auxiliary input device 109 (e.g., an audio input port, a cable port, a telecoil, etc.). If not already in an electrical form, input devices 113 convert received/input sound signals into electrical signals 153, referred to herein as electrical sound signals, which represent the sound signals received at the input devices 113. As shown in FIG. 3, the electrical sound signals 153 include electrical sound signal 153A from microphone 108A, electrical sound signal 153B from microphone 108B, and electrical sound signal 153C from auxiliary input 109.

Also as noted above, the cochlear implant 100 comprises the processing module 125 which includes, among other elements, sound processing logic 133, classifier-based feature extraction logic 134, and feature-based adjustment logic 135. The sound processing logic 133, when executed by the one or more processors 130, enables the processing module 125 to perform sound processing operations that convert sound signals into stimulation control signals for use in delivery of stimulation to the recipient. In FIG. 3, the functional operations enabled by the sound processing logic 133 (i.e., the operations performed by the one or more processors 130 when executing the sound processing logic 133) are generally represented by modules 154, 156, 158, 160, and 162, which collectively comprise a sound processing path 151. The sound processing path 151 comprises a pre-filterbank processing module 154, a filterbank module (filterbank) 156, a post-filterbank processing module 158, a channel selection module 160, and a channel mapping and encoding module 162, each of which are described in greater detail below.

More specifically, the electrical sound signals 153 generated by the input devices 113 are provided to the pre-filterbank processing module 154. The pre-filterbank processing module 154 is configured to, as needed, combine the electrical sound signals 153 received from the input devices 113 and prepare/enhance those signals for subsequent processing. The operations performed by the pre-filterbank processing module 154 may include, for example, microphone directionality operations, noise reduction operations, input mixing operations, input selection/reduction operations, dynamic range control operations and/or other types of signal enhancement operations. The operations at the pre-filterbank processing module 154 generate a pre-filterbank output signal 155 that, as described further below, is the basis of further sound processing operations. The pre-filterbank output signal 155 represents the combination (e.g., mixed, selected, etc.) of the input signals (e.g., mixed, selected, etc.) received at the sound input devices 113 at a given point in time.

In operation, the pre-filterbank output signal 155 generated by the pre-filterbank processing module 154 is provided to the filterbank module 156. The filterbank module 156 generates a suitable set of bandwidth limited channels, or frequency bins, that each includes a spectral component of the received sound signals. That is, the filterbank module 156 comprises a plurality of band-pass filters that separate the pre-filterbank output signal 155 into multiple components/channels, each one carrying a frequency sub-band of the original signal (i.e., frequency components of the received sounds signal).

The channels created by the filterbank module 156 are sometimes referred to herein as sound processing channels, and the sound signal components within each of the sound processing channels are sometimes referred to herein as band-pass filtered signals or channelized signals. The band-pass filtered or channelized signals created by the filterbank module 156 are processed (e.g., modified/adjusted) as they pass through the sound processing path 151. As such, the band-pass filtered or channelized signals are referred to differently at different stages of the sound processing path 151. However, it will be appreciated that reference herein to a band-pass filtered signal or a channelized signal may refer to the spectral component of the received sound signals at any point within the sound processing path 151 (e.g., pre-processed, processed, selected, etc.).

At the output of the filterbank module 156, the channelized signals are initially referred to herein as pre-processed signals 157. The number 'm' of channels and pre-processed signals 157 generated by the filterbank module 156 may depend on a number of different factors including, but not limited to, implant design, number of active electrodes, coding strategy, and/or recipient preference(s). In certain arrangements, twenty-two (22) channelized signals are created and the sound processing path 151 is said to include 22 channels.

The pre-processed signals 157 are provided to the post-filterbank processing module 158. The post-filterbank processing module 158 is configured to perform a number of sound processing operations on the pre-processed signals 157. These sound processing operations include, for example, channelized gain adjustments for hearing loss compensation (e.g., gain adjustments to one or more discrete frequency ranges of the sound signals), noise reduction operations, speech enhancement operations, etc., in one or more of the channels. After performing the sound processing operations, the post-filterbank processing module 158 outputs a plurality of processed channelized signals 159.

In the specific arrangement of FIG. 3, the sound processing path 151 includes a channel selection module 160. The channel selection module 160 is configured to perform a channel selection process to select, according to one or more selection rules, which of the 'm' channels should be use in hearing compensation. The signals selected at channel selection module 160 are represented in FIG. 3 by arrow 161 and are referred to herein as selected channelized signals or, more simply, selected signals.

In the embodiment of FIG. 3, the channel selection module 156 selects a subset 'n' of the 'm' processed channelized signals 159 for use in generation of electrical stimulation for delivery to a recipient (i.e., the sound processing channels are reduced from 'm' channels to 'n' channels). In one specific example, the 'n' largest amplitude channels (maxima) from the 'm' available combined channel signals is made, with 'm' and 'n' being programmable during initial fitting, and/or operation of the prosthesis. It is to be appreciated that different channel selection methods could be used, and are not limited to maxima selection. It is also to be appreciated that, in certain embodiments, the channel selection module 160 may be omitted. For example, certain arrangements may use a continuous interleaved sampling (CIS), CIS-based, or other non-channel selection sound coding strategy.

The sound processing path 151 also comprises the channel mapping module 162. The channel mapping module 162 is configured to map the amplitudes of the selected signals 161 (or the processed channelized signals 159 in embodiments that do not include channel selection) into a set of stimulation control signals (e.g., stimulation commands) that represent the attributes of the electrical stimulation signals that are to be delivered to the recipient so as to evoke perception of at least a portion of the received sound signals. This channel mapping may include, for example, threshold and comfort level mapping, dynamic range adjustments (e.g., compression), volume adjustments, etc., and may encompass selection of various sequential and/or simultaneous stimulation strategies.

In the embodiment of FIG. 3, the set of stimulation control signals (stimulation commands) 136 that represent the electrical stimulation signals are encoded for transcutaneous transmission (e.g., via an RF link) to an implantable component 104 as the stimulation control signals 136 (FIG. 1B). This encoding is performed, in the specific example of FIG. 3, at the channel mapping module 162. As such, channel mapping module 162 is sometimes referred to herein as a channel mapping and encoding module and operates as an output block configured to convert the plurality of channelized signals into a plurality of stimulation control signals 136.

As noted, the sound processing path 151 generally operates to convert received sound signals into stimulation control signals 136 for use in delivering stimulation to the recipient in a manner that evokes perception of the sound signals. In certain examples, the stimulation control signals 136 may include one or more adjustments (enhancements) that are based on specific "signal features" ("features") of the received sound signals. That is, the processing module 125 is configured to determine one or more "feature-based" adjustments for incorporation into the stimulation control signals 136, where the one or more feature-based adjustments are incorporated at one or more points within the processing path 151 (e.g., at module 158). The feature-based adjustments may take a number of different forms. For example, one or more measures of fundamental frequency (F0) (e.g., frequency or magnitude) may be extracted from the received sound signals and then used to apply an enhancement within the sound processing path such that the F0 present in the sound signals is incorporated into the stimulation control signals 136 in a manner that produces a more salient pitch percept to the recipient. Henceforth the percept of pitch elicited by the acoustic feature F0 in the sounds signals is referred to as "F0-pitch".

As noted, different feature-based adjustments may be incorporated into a sound processing path, such as sound processing path 151. However, in accordance with embodiments presented herein, an element of each of these adjustments is that the adjustments are all made based on one or more "signal features" and, as describe further below, the feature-based adjustments in accordance with embodiments presented herein are controlled at least partially based on an environmental classification of the sound signals. As used herein, a "signal feature" or "feature" of a received sound signal refers to an acoustic property of the signal that has a perceptual correlate. For instance, intensity is an acoustic signal property that affects perception of loudness, while the fundamental frequency (F0) of an acoustic signal (or set of signals) is an acoustic property of the signal that affects perception of pitch. In other examples, the signal features may include, for example, other percepts or sensations (e.g., the first formant (F1) frequency, the second formant (F2) frequency), and/or other formants), other harmonicity measures, rhythmicity measures, measures regarding the static and/or dynamic nature of the sound signals, etc. As described further below, these or other signal features may be extracted and used as the basis for one or more feature-based adjustments for incorporation into the stimulation control signals 136.

In order to incorporate feature-based adjustments into the stimulation control signals 136, the one or more signal features that form the basis for the adjustment(s) need to first be extracted from the received sound signals using a feature extraction process. Certain embodiments presented herein are directed to techniques for controlling/adjusting one or more parameters of the feature extraction process based on a sound environment of the input sound signals. As described further below, controlling/adjusting one or more parameters of the feature extraction process based on the sound environment tailors/optimizes the feature extraction process for the current/present sound environment, thereby improving the feature extraction processing (e.g., increasing the likelihood that the signal features are correctly identified and extracted) and improving the feature-based adjustments, which ultimately improves the stimulation control signals 136 that are used for generation of stimulation signals for delivery to the recipient.

Merely for ease of illustration, further details of the techniques presented herein will generally be described with reference to extraction and use of one specific signal feature, namely the fundamental frequency (F0) and its perceptual correlate (F0-pitch) of the received sound signal. The fundamental frequency is the lowest frequency of vibration in a sound signal such as a voiced-vowel in speech or a tone played by a musical instrument (i.e., the rate at which the periodic shape of the signal repeats). In these illustrative examples, the feature-based adjustment incorporated into the sound processing path is an F0-pitch enhancement where the amplitudes of the signals in certain channels are modulated at the F0 frequency, thereby improving the recipient's perception of the F0-pitch. It is to be appreciated that specific reference to the extraction and use of the F0 frequency (and the subsequent F0-pitch enhancement) is merely illustrative and, as such, the techniques presented herein may be implemented to extract other features of sound signals for use in feature-based adjustments. For example, extracted signal features may include the F0 harmonic frequencies and magnitudes, non-harmonic signal frequencies and magnitudes, etc.

Returning to the specific example of FIG. 3, shown is an environmental classifier 164 that is also configured to receive the electrical sound signals 153 generated by the microphone 108A, microphone 108B, and/or auxiliary input 109 (i.e., the electrical sound signals 153 are directed to both the pre-filterbank processing module 154 and the environmental classifier 164). The environmental classifier 164 represents the functional operations enabled by the classifier logic 131 of FIG. 1B (i.e., the operations performed by the one or more processors 130 when executing the classifier logic 131). The environmental classifier 164 is configured to "classify" or "categorize" the sound environment of the sound signals received at the input devices 113. The environmental classifier 164 may be configured to categorize the sound environment into a number of classes/categories. In one illustrative example, the environmental classifier 164 may be configured to categorize the sound environment into one of six (6) categories, including "Speech," "Noise," "Speech in Noise," "Music," "Wind," and "Quiet." In general, the environmental classifier 164 operates to determine a category of for the sound signals using a type of decision structure (e.g., decision tree, alternative machine learning designs/approaches, and/or other structures that operate based on individual extracted characteristics from the input signals).

The category of the sound environment associated with the sound signals may be used to adjust one or more settings/parameters of the sound processing path 151 for different listening situations or environments encountered by the recipient, such as noisy or quiet environments, windy environments, or other uncontrolled noise environments. In FIG. 3, arrows 163 generally illustrate that different operating parameters of one or more of the modules 154, 156, 158, 160, and/or 162 could be adjusted for operation in different sound environments.

In accordance with embodiments of the present invention, in addition to controlling sound processing operations of the signal processing path 151, the environmental classifier 164 may also be configured to optimize extraction of the features used for feature-based adjustments included in the signal processing path 151. As noted above, the processing module 125 includes classifier-based feature extraction logic 134 that, when executed by the one or more processors 130, enables the processing module 125 to extract one or more features of the sound signals. In FIG. 3 the functional operations enabled by the classifier-based feature extraction logic 134 (i.e., the feature extraction operations performed by the one or more processors 130 when executing the classifier-based feature extraction logic 134) are generally represented by feature extraction pre-processing module 166 and feature extraction module 168. As such, the feature extraction pre-processing module 166 and feature extraction module 168 are generally referred to herein as performing feature-extraction operations of a feature extraction process.

Also as noted above, the processing module 125 includes feature-based adjustment logic 135 that, when executed by the one or more processors 130, enables the processing module 125 to generate, from extracted signal features, one or more signal adjustments for incorporation into the sound processing path 151. In FIG. 3 the functional operations enabled by the feature-based adjustment logic 135 (i.e., the operations performed by the one or more processors 130 when executing the feature-based adjustment logic 135) are represented by feature-based adjustment module 170. The feature extraction pre-processing module 166, feature extraction module 168, and feature-based adjustment module 170 collectively form a feature adjustment processing path 173 that is separate from, and runs in parallel to, the signal processing path 151. As such, the feature extraction pre-processing module 166 separately receives the electrical sound signals 153 generated by the microphone 108A, microphone 108B, and/or auxiliary input 109.

The feature extraction pre-processing module 166 may be configured to perform operations that are similar to the pre-filterbank processing module 154. For example, the pre-processing module 166 may be configured to perform microphone directionality operations, noise reduction operations, input mixing operations, input selection/reduction operations, dynamic range control operations, and/or other types of signal enhancement operations. However, in the embodiment of FIG. 3, the operations performed at feature extraction pre-processing module 166 are selected/controlled by the environmental classifier 164 in a manner that optimizes extraction of the desired signal feature(s), such as the F0 frequency. As such, the operations of the feature extraction pre-processing module 166 are sometimes referred to herein as feature-extraction pre-processing operations. In FIG. 3, control of one or more parameters of the feature extraction process (i.e., control of parameters of the feature extraction pre-processing module 166 and/or the feature extraction module 168) by the environmental classifier 164 is generally represented in FIG. 3 by arrows 165.

The present applicants have determined that different sound environments may affect the quality of the signal feature(s) extracted from the sound signals. As such, in certain embodiments, the environment classifier 164 controls which feature-extraction pre-processing operations are, or are not, performed on the sound signals before the extraction of the signal features therefrom to improve the feature extraction process (e.g., increasing the likelihood that the signal features are correctly identified and extracted). The operations of the feature extraction pre-processing module 166, which are at least partially controlled by the environmental classifier 164, result in the generation of a pre-processed signal that is provided to the feature extraction module 168. The pre-processed signal is generally represented in FIG. 3 by arrow 167. The feature extraction module 168 performs one or more operations to extract the target/desired signal feature(s) from the pre-processed signal 167.

As represented by arrow 169, the extracted features obtained by the feature extraction module 168 are provided to the feature-based adjustment module 170. The feature-based adjustment module 170 then performs one or more operations to generate a feature-based adjustment for incorporation into the signal processing path 151 and, accordingly, into the stimulation control signals 136.

In summary, FIG. 3 illustrates an embodiment in which two processing paths operate in parallel. The first processing path, referred to above as the signal processing path 151, uses sound processing operations to convert the received sound signals in stimulation control signals 136. The sound processing operations of the signal processing path 151 are all controlled/adjusted so as to optimize the recipient's perception of the sound signals received via the input devices 113. In contrast, the second processing path, referred to above as the feature adjustment processing path 173, includes feature extraction operations that are controlled/selected so as to optimize the feature extraction process based on the sound environment of the sound signals received via the input devices 113 and to incorporate a feature-based adjustment into the stimulation control signals 136. With reference to the feature adjustment processing path 173, the environmental classifier 164 operates to control one or more parameters of the feature extraction operations (e.g., at 166 and/or 168).

Further understanding of the embodiment of FIG. 3 may be appreciated through the description of several illustrative use cases relating to extraction and use of the F0 frequency. For example, the present applicant has discovered that the extraction of the F0 frequency can be more difficult in certain sound environments than in other sound environments. For example, consider a situation in which a tonal language (e.g., Mandarin) speaking recipient is located in a noisy café in China and is attempting to converse with another individual. In this example, the environment classifier 164 determines that recipient is located in a "Speech in Noise" environment (i.e., the sound signals detected by the microphones 108A and 108B are "Speech in Noise" signals). As a result of this determination, the environment classifier 164 configures the pre-filterbank processing module 154 to perform microphone beamforming to optimize listening from directly in front of the recipient, and to perform Background Noise Reduction. Also as a result of the "Speech in Noise" classification, the environment classifier 164 configures the feature extraction pre-processing module 166 to perform a specific microphone beamforming that optimizes the extraction of the F0 frequency.

Now consider a recipient attending a music concert. In this example, the environment classifier 164 determines that recipient is located in a "Music" environment. As a result of this determination, the environment classifier 164 configures the pre-filterbank processing module 154 to a "Moderate" microphone directionality, which is only partly directional allowing for sound input from a broad area ahead of the recipient. Also a result of the "Music" classification, the environment classifier 164 configures the feature extraction pre-processing module 166 to an omnidirectional microphone setting, which again is a broad area of input, from all around the recipient.

The above two examples illustrate two specific techniques in which the environment classifier 164 adjusts the operations of the feature extraction pre-processing module 166 to optimize the ability to extract the F0 frequency information from the input, based on the sound environment. More generally, in accordance with certain embodiments presented herein, the environment classifier 164 operates to control what operations are, or are not, performed on the sound signals (i.e., electrical signals 153) feature extraction of one or more signal features therefrom in accordance with (i.e., based on) the sound environment of the received sound signals. As can be seen from the above two examples, the specific feature-extraction pre-processing operations performed at the feature extraction pre-processing module 166 may be different from the operations performed at the pre-filterbank processing module 154 because the goals/intents of the two modules are different (i.e., the pre-filterbank processing module 154 is configured to prepare the sound signals for sound processing and conversion to the stimulation commands while the feature extraction pre-processing module 166 is configured to prepare the sound signals for feature extraction).

FIG. 3 illustrates an example in which the environmental classifier 164 is configured to control/adjust operations of the feature extraction process (i.e., one or more parameters of one or more of the feature extraction operations at 166 and/or 168 are adjusted at least partially based on an environmental classification of the current sound environment). It is to be appreciated that, similar to the embodiments described further below with reference to FIGS. 6A, 6B, and 7, that signal 165 could also be used as an input to the feature based adjustment module 170 (i.e., to control one or more parameters of the operations at 170).

As noted, FIG. 3 illustrates an example in which the environmental classifier 164 is configured to control/adjust operations of both the sound processing path 151 and the feature adjustment processing path 173. As such, the environmental classifier 164 is a dual-mode (dual-function) environmental classifier configured to run multiple processes that optimize both the control signals 136 and extraction of the desired feature(s). It is to be appreciated that this dual-mode functionality of the environmental classifier is illustrative and that an environmental classifier in accordance with embodiments presented herein may be configured with further functionality or may be configured to perform a single function.

Figure 4:
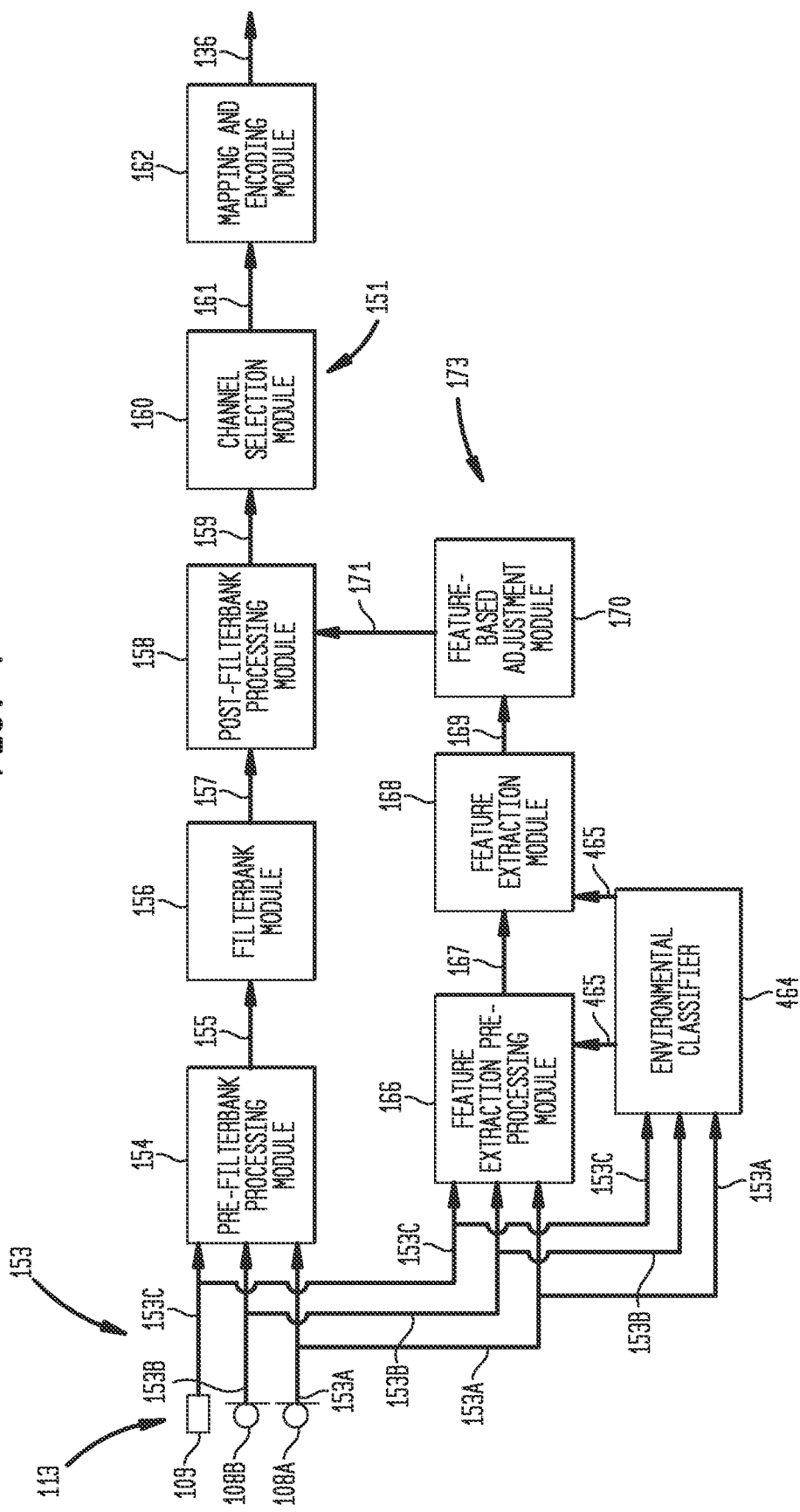
FIG. 4 is a functional block diagram illustrating further details of a hearing prosthesis configured to implement certain techniques presented herein.

For example, FIG. 4 is a functional block diagram illustrating another example arrangement for the sound processing unit 112 of cochlear implant 100. For ease of illustration, elements that are not related to the sound processing or the classifier-based feature extraction techniques have been omitted from FIG. 4.

In the embodiment of FIG. 4, the sound processing unit 112 has an arrangement that is substantially similar to the arrangement of FIG. 3. However, in the embodiment of FIG. 4, the dual-mode environmental classifier 164 of FIG. 3 is replaced by an environmental classifier 464 that is configured to only control one or more parameters of one or more operations of the feature extraction process (e.g., one or more parameters of the operations performed at the feature-extraction pre-processing module 166 and/or the feature extraction module 168). That is, in the embodiment of FIG. 4, the environmental classifier 464 operates solely to optimize the extraction of the desired feature(s) within the feature adjustment processing path 173, but does not control operations of the sound processing path 151. In FIG. 4, control of the feature extraction pre-processing module 166 and/or feature extraction module 168 is represented by arrows 465.

FIG. 5 is a functional block diagram illustrating another example arrangement for the sound processing unit 112 of cochlear implant 100. For ease of illustration, elements that are not related to the sound processing or the classifier-based feature extraction techniques have been omitted from FIG. 5.

In the embodiment of FIG. 5, the sound processing unit 112 has an arrangement that is substantially similar to the arrangement of FIG. 4 where the environmental classifier 464 operates solely to optimize the extraction of the desired feature(s) within the feature adjustment processing path 173, but does not control operations of the sound processing path 151. However, in the embodiment of FIG. 5 a second environmental classifier 564 is added that is configured to only control operations of the sound processing path 151 (i.e., operates solely to adjust operations of one or more of optimize the control signals 136 for the sound environment). More specifically, in the embodiment of FIG. 5, the environmental classifier 564 receives the electrical signals 153 generated by one or more of the input devices 113 (based on the received sound signals). The environmental classifier 564 operates to classify the sound environment associated with the received sound signals and, based on this classification, control one or more parameters of the one or more operations performed at the modules 154, 156, 158, 160, and/or 162. Control of the operations of the modules 154, 156, 158, 160, and/or 162 is generally represented in FIG. 5 by arrows 563.

In summary, FIG. 5 illustrates an embodiment comprising two separate and distinct environmental classifiers, where one classifier is configured to at least partially control extraction of one or more signal feature extraction tasks (i.e., control/adjust one or more parameters of the feature extraction process), and the other classifier is configured to assist with the regular operation of the sound processing path (i.e., control one or more parameters of the sound processing operations). In this embodiment, the two classifiers do not need to have any link to one another, and may be designed completely differently, as their goals are different.

Figure 6A:
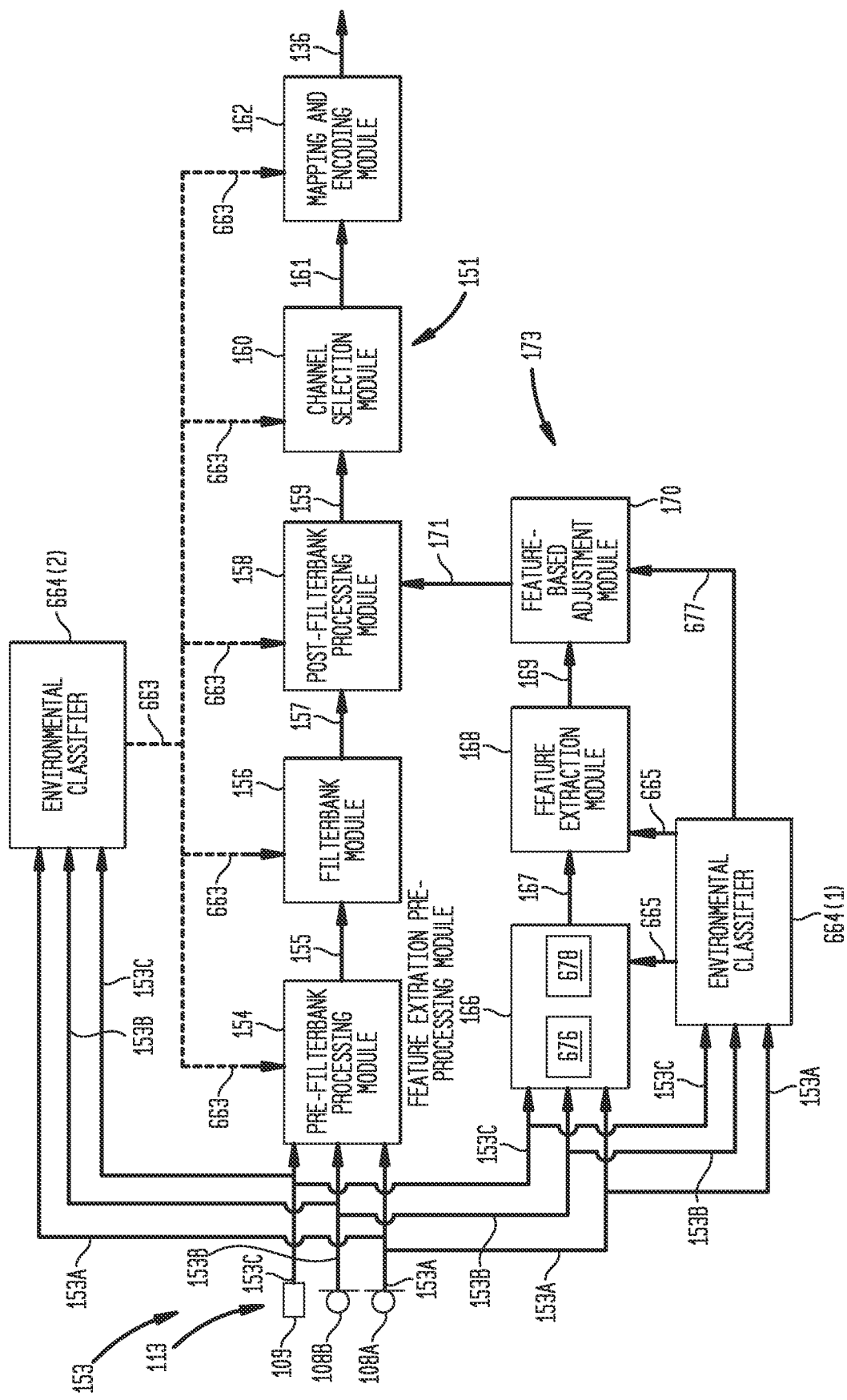
FIG. 6A is a functional block diagram illustrating further details of a hearing prosthesis configured to implement certain techniques presented herein.

FIGS. 3, 4, and 5 generally illustrate embodiments in which an environmental classifier is used to control extraction of features from sound signals for use in feature-based adjustment processes/operations. In further embodiments presented herein, an environmental classifier may also be used to control the feature-based adjustment operations. FIG. 6A is a functional block diagram illustrating one such arrangement.

More specifically, FIG. 6A illustrates an arrangement for the sound processing unit 112 of cochlear implant 100 that is similar to the arrangement of FIG. 5 where two environmental classifiers, referred to as environmental classifier 664(1) and environmental classifier 664(2), are provided. The environmental classifier 664(2) receives the electrical signals 153 generated by one or more of the input devices 113 (based on the received sound signals). The environmental classifier 664(2) operates to classify the sound environment associated with the received sound signals and, based on this classification, control one or more parameters of one or more operations performed at the modules 154, 156, 158, 160, and/or 162. Control of the operations of the modules 154, 156, 158, 160, and/or 162 is generally represented in FIG. 6A by arrows 663.

The environmental classifier 664(1) operates, similar to the above embodiments, to optimize the extraction of the desired feature(s) within the feature adjustment processing path 173 (i.e., to control one or more parameters of the one or more feature extraction operations, as represented by arrows 665). In this example, the feature extraction pre-processing module 166 includes a dynamic range compression module 676 and a voice activity detector (VAD) 678. The dynamic range compression module 676 is configured to perform aggressive dynamic range compression, which differs by environment, such that there is minimal, or no difference in long-term signal level (i.e., the environmental classifier 664(1) controls the applied dynamic range compression based on the environmental classification). As a result, the voice activity detector 678 will detect voice activity, regardless of environment or the loudness of the voice presents in the sound signals.

In addition to controlling the feature extraction pre-processing at module 166, the environmental classifier 664(1) of FIG. 6A is also configured to control the feature-based adjustment operations implemented at the feature-based adjustment module 170. In other words, the environmental classifier 664(1) operates to control one or more parameters of the operations of the feature-based adjustment module 170 (i.e., one or more parameters of the feature-based adjustment determination) based on the environmental classification made by the classifier. Control of the feature-based adjustment module 170 is generally represented in FIG. 6A by arrow 677.

Further understanding of the embodiment of FIG. 6A may be appreciated through description of several illustrative use cases relating to extraction and use of the F0 frequency. Again consider a situation in which a tonal language (e.g., Mandarin) speaking recipient is located in a noisy café in China and is attempting to converse with another individual. In this example, the environment classifier 664(1) determines that recipient is located in a "Speech in Noise" environment. As result of this "Speech in Noise" classification, the environment classifier 664(1) configures the feature extraction pre-processing module 166 to perform a specific microphone beamforming that optimizes the extraction of the F0 frequency. In addition, in this example, the feature-based adjustment performed at module 170 is configured to modulate the signals within one or more channels with the F0 frequency, thereby enhancing the perception of the F0-pitch by the recipient. Given the "Speech in Noise" classification, the environment classifier 664(1) configures the feature-based adjustment performed at module 170 to operate in accordance with a "moderate" or "medium" setting in which the F0 frequency modulation is moderately applied to one or more channels. In on example, a "moderate" setting of pitch enhancement would provide 50% of the possible enhancement range (e.g., F0 modulation that spans 50% (half) of electrical channel signals' dynamic range).

Now consider a recipient attending a music concert. In this example, the environment classifier 164 determines that recipient is located in a "Music" environment. As result of this "Music" classification, the environment classifier 664(1) configures the feature extraction pre-processing module 166 to an omnidirectional microphone setting. In addition, in this example, the feature-based adjustment performed at module 170 is again configured to modulate the signals within one or more channels with the F0 frequency, thereby enhancing the perception of the F0-pitch by the recipient. Given the "Music" classification, the environment classifier 664(1) configures the feature-based adjustment performed at module 170 to operate in accordance with a "maximum" setting in which the F0 frequency modulation is strongly applied to one or more channels. In on example, a "maximum" setting of pitch enhancement would provide 100% of the possible enhancement range (e.g., F0 modulation that spans 100% (all) of electrical channel signals' dynamic range).

The above two examples illustrate two specific techniques in which the environment classifier 664(1) controls/adjusts one or more parameters of one or more feature-based adjustment operations performed at module 170 to optimize the perception of the F0-pitch information by the recipient, based on the sound environment. More generally, in accordance with certain embodiments presented herein, the environment classifier 664(1) operates to control the feature-based adjustments for incorporation into the sound processing path in accordance with (i.e., at least partially based on) the sound environment of the received sound signals.

As noted, FIG. 6A has been described with reference to the presence of two independent classifiers. It is to be appreciated that the presence of two classifiers is illustrative and that, in alternative embodiments, the classifier 664(2) could be omitted. In one such embodiment, the classifier 664(1) may also be configured to control one or more parameters of the sound processing operations performed at one or more of the modules 154, 156, 158, 160, and/or 162.

As noted above, embodiments of the present invention are generally directed to techniques for determination a feature-based adjustment for incorporation into stimulation control signals, where the feature-based adjustment is at least partially controlled/adjusted based on the current sound environment. FIGS. 3, 4, 5, and 6A generally illustrate embodiments in which a classification of the current sound environment is used to control the feature extraction process (e.g., one or more parameters of the pre-processing operations at a feature-extraction pre-processing module 166 and/or one or more parameters of the feature-extraction process at a feature-extraction module 168). FIG. 6A illustrates that, in addition to control of the feature extraction process, a classification of the current sound environment may also be used to control the feature-based adjustment operations (i.e., one or more parameters of the feature-based adjustment determination at a feature-based adjustment module 170). FIG. 6B illustrates another arrangement in which the classification of the current sound environment is used to only control the feature-based adjustment operations.

More specifically, the arrangement shown in FIG. 6B is similar to the arrangement shown in FIG. 6A, except that the environmental classifier 664(1) does not provide any inputs to the feature extraction process. That is, the environmental classifier 664(1) does not operate to control any parameters of either the feature-extraction pre-processing module 166 or the feature-extraction module 168. As a result, both the pre-processing and the feature extraction operations are independent of the environmental classification.

However, as shown in FIG. 6B, the environmental classifier 664(1) still provides input 677 to the feature-based adjustment module 170. In this embodiment, the input 677 is used to indicate whether the feature-based adjustment module 170 should use or ignore the input 169 (i.e., extracted features) received from the feature-extraction module 168. For example, the feature-based adjustment module 170 may be instructed (via input 677) to ignore the output when the environmental classifier 664(1) determines that the sound environment is "noise" or "speech in noise," but could be instructed to use the output in other sound environments.

FIG. 7 is a functional block diagram illustrating yet another arrangement for the sound processing unit 112 of cochlear implant 100 that incorporates user control. The embodiment of FIG. 7 is similar to the arrangement of FIG. 7 where two environmental classifiers, referred to as environmental classifier 764(1) and environmental classifier 764(2), are provided. Classifier 764(2) operates to classify the sound environment associated with the received sound signals and, based on this classification, control one or more parameters of one or more of the operations performed at the modules 154, 156, 158, 160, and/or 162. Control of the operations of the modules 154, 156, 158, 160, and/or 162 is generally represented in FIG. 7 by arrows 763. The environmental classifier 764(1) operates, similar to environmental classifier 664(1) of FIG. 6, to control one or more parameters of the one or more feature extraction operations within the feature adjustment processing path 173 (as represented by arrows 765). In addition, the environmental classifier 764(1) of FIG. 7 is also configured to control one or more parameters of the feature-based adjustment operations implemented at the feature-based adjustment module 170 (as represented by arrow 777).

In addition, the embodiment of FIG. 7 includes a user control module 780 (e.g., user interface) that enables the environmental classifier 764(1) to receive user preference information. For example, in terms of providing a suitable pitch enhancement setting to match the environment, the user control module 780 provides the environmental classifier 764(1) with a user preference setting or other indications such as the probability that the input signal is a harmonic complex signal related to the estimated F0. These additional considerations could be multiplied (and/or weighted) with the detected environment, in order to determine the final enhancement setting.

For example, in one example F0-pitch enhancement strategy, an estimate of the harmonic signal power-to-total power ratio (STR) is utilized as a metric to the probability of the sound input being a harmonic (voiced/musical) signal that is harmonically related to the estimated F0 frequency. As such, the STR it is used to programmatically control the overall degree of pitch enhancement applied by adjustment of the F0 modulation depth applied to the channel signals.

Figure 8:
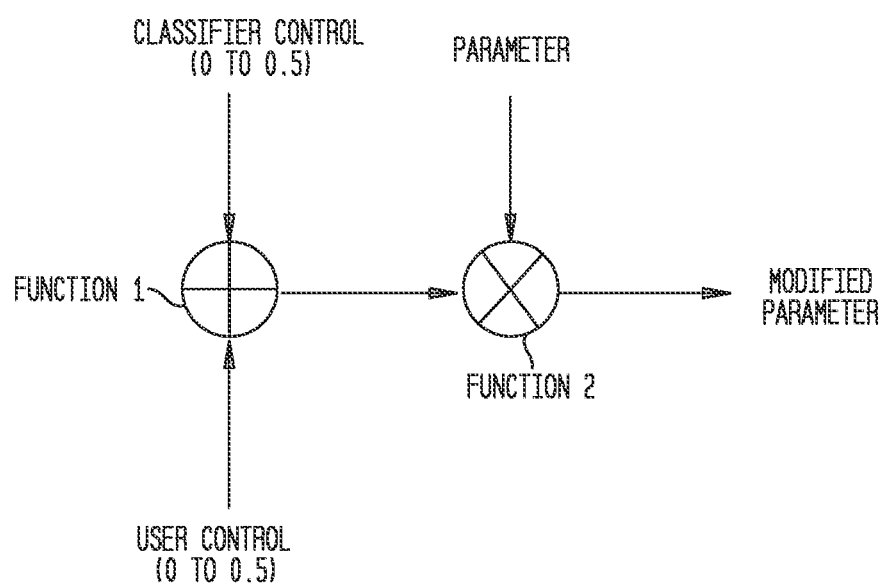
FIG. 8 is a schematic diagram illustrating control of the degree of pitch enhancement applied during sound processing, in accordance with certain embodiments presented herein.

In the embodiment of FIG. 7, the degree of pitch enhancement applied (either through program or user control) could be further adjusted for example, by scaling the estimated STR value appropriately. For instance, when pitch enhancement is set to maximum by the classifier (and/or user), the scaler would be unity thereby allowing the degree of pitch enhancement applied to be based solely on the probability that the input is a complex harmonic signal (i.e., on the estimated STR). In contrast, when pitch enhancing is set to minimum, the scaler could be set to 0.5 (or even 0), thereby forcing the degree of enhancement applied to be minimal (to none). Such an arrangement is shown on FIG. 8. In this example, the user control and the classifier operate in conjunction (i.e., summed) with one another. Other embodiments of the techniques presented herein could apply different functions or combinations of functions to implement various configurations of classifier/user control for modification of parameters.

Returning to FIG. 7, other feature-based adjustments, such as other F0-pitch enhancement parameters, could also be at least partially controlled by the classifier and or a user. For instance, the classifier could at least partially control parameters such as the F0 restore gain (which is the amount of additional gain applied in each channel based on its harmonic probability), the shape and depth of the F0 modulation function applied, and the number of multiplexed maxima. Furthermore, enhancement of other speech features unrelated to the F0-pitch enhancements, such as vowel formant frequencies and amplitudes, and speech envelope dynamics, or strategy parameters such as multi-channel compression/expansion and stimulation timing could also be at least partially controlled by the classifier. Enhanced/controlled features also need not be limited to speech but could include features of musical sounds, such as resonant frequencies of instruments, amplitude envelope dynamics, etc.

In certain embodiments of FIG. 7, the environmental classifier 764(1) may also incorporate a trainable component in which decisions made by the detected class are trained or modified via user input. For example, if a manual control for F0-pitch enhancement is provided to the user, the trainable component of the classifier can observe how the user controls this parameter and try to duplicate this behavior. If the user always sets the enhancement to "maximum" when in a music scene, the classifier can learn this and automatically set this setting when music is detected. In this case the user control is employed as an input voting device (e.g., binary, categorical, or numerical) to the trainable component which itself is used to control adjustment of one or more program parameters in conjunction with the classifier.

Figure 9:
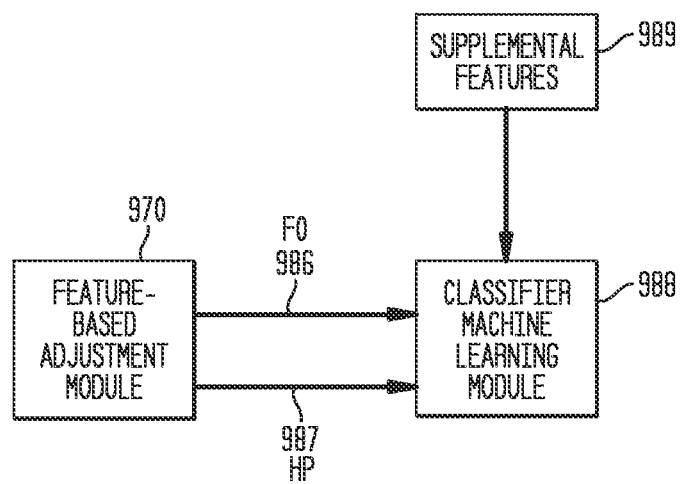
FIG. 9 is a functional block diagram illustrating feature-based training of an environmental classifier, in accordance with certain embodiments presented herein.

Extending upon the above, an environmental classifier could be trained based using the features that are used by a feature-based adjustment process, thereby making the classifier more robust. FIG. 9 illustrates one specific example of using two features used during one specific feature-based adjustment process.

More specifically, FIG. 9 illustrates an example in which a feature-based adjustment module 970 provides the fundamental frequency (F0) 986 and harmonic probability (HP) 987 to a classifier machine learning module 988. The classifier machine learning module 988 is configured to use the F0 and HP to train an environmental classifier (not shown in FIG. 9). By adding the F0 and HP features to the environment classifier, the existing classifier algorithm can be retrained (using the offline machine learning) to deliver higher accuracy across its classes. After training, classification is more accurate, so pitch enhancement can be automated with more reliability.

An environmental classifier could also be trained using supplemental signal features 989. For example, with the addition of learning harmonic probability measures and an understanding of voiced-speech pitch ranges of training data, a speech classifier may exhibit higher performance. A music classifier or noise classifier may also be improved.

FIG. 10 is a flowchart of a method 1090 performed at a hearing prosthesis, in accordance with certain embodiments presented herein. Method 1090 begins at 1091 where the hearing prosthesis receives one or more sound signals. At 1092, the hearing prosthesis determines, from the one or more sound signals, an environmental classification of a current sound environment associated with the one or more sound signals. At 1093, the hearing prosthesis performs one or more feature-extraction operations to extract at least one signal feature from the one or more sound signals, where the one or more feature-extraction operations are controlled at least partially based on the environmental classification of the current sound environment.

FIG. 11 is a flowchart of a method 1194 performed at a hearing prosthesis, in accordance with certain embodiments presented herein. Method 1194 begins at 1195 where the hearing prosthesis receives at least one sound signal. At 1196, the hearing prosthesis determines, from the at least one sound signal, an environmental classification of a current sound environment associated with the at least one sound signal. At 1197, the hearing prosthesis converts the at least one sound signal into stimulation control signals for use in stimulating a recipient of the hearing prosthesis. At 1198, the hearing prosthesis extracts, using a feature extraction process, one or more signal features from the at least one sound signal, wherein one or more parameters of the feature extraction process are controlled based on the environmental classification of the current sound environment. At 1199, the hearing prosthesis determines at least one feature-based adjustment for incorporation into the stimulation control signals, wherein the at least one feature-based adjustment is based on at least one of the one or more features extracted from the at least one sound signal.

Figure 12:
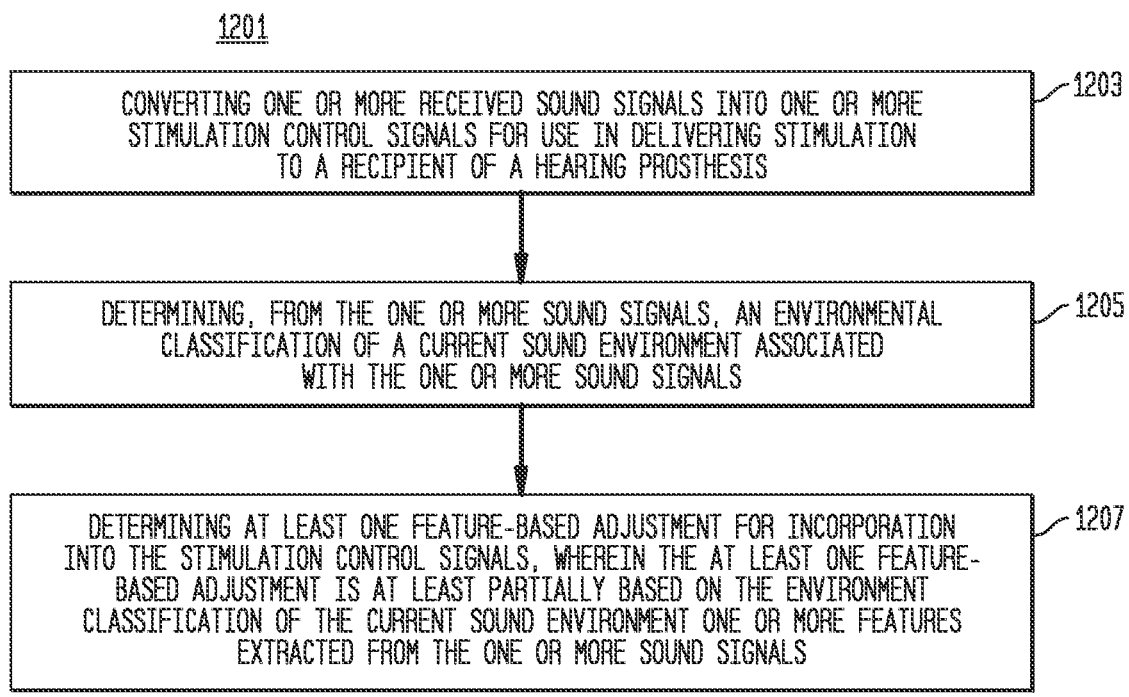
FIG. 12 is another flowchart of a method, in accordance with certain embodiments presented herein.

FIG. 12 is a flowchart of a method 1201 performed at a hearing prosthesis, in accordance with certain embodiments presented herein. Method 1201 begins at 1203 where the hearing prosthesis converts one or more received sound signals into one or more stimulation control signals for use in delivering stimulation to a recipient of the hearing prosthesis. At 1205, the hearing prosthesis determines, from the one or more sound signals, an environmental classification of a current sound environment associated with the one or more sound signals. At 1207, the hearing prosthesis determines at least one feature-based adjustment for incorporation into the stimulation control signals, wherein the at least one feature-based adjustment is at least partially based on the environmental classification of the current sound environment at least one of the one or more features extracted from the one or more sound signals.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
receiving one or more input signals at a hearing device;
determining, from the one or more input signals, an environmental classification of a current ambient environment associated with the one or more input signals; and
performing one or more feature-extraction operations to extract at least one signal feature from the one or more input signals,
wherein the one or more feature-extraction operations are controlled at least partially based on the environmental classification of the current ambient environment.

2. The method of claim 1, further comprising:
generating, from the one or more input signals, stimulation control signals for use in stimulating a recipient of the hearing device; and
incorporating at least one feature-based adjustment into the stimulation control signals, wherein the at least one feature-based adjustment is based on the at least one signal feature extracted from the one or more input signals.

3. The method of claim 2, wherein incorporating the at least one feature-based adjustment into the stimulation control signals comprises:
executing one or more feature-based adjustment operations to determine the at least one feature-based adjustment for incorporation into the stimulation control signals, wherein the one or more feature-based adjustment operations are adjusted at least partially based on the environmental classification of the current ambient environment.

4. The method of claim 1, wherein performing the one or more feature-extraction operations to extract the at least one signal feature from the one or more input signals comprises:
performing one or more feature-extraction pre-processing operations on the one or more input signals to generate one or more pre-processed signals;
extracting the at least one signal feature from the one or more pre-processed signals; and
adjusting the one or more feature-extraction pre-processing operations at least partially based on the environmental classification of the current ambient environment.

5. The method of claim 4, further comprising:
generating, from the one or more input signals, stimulation control signals for use in stimulating a recipient of the hearing device,
wherein the one or more feature-extraction pre-processing operations and the extracting of the at least one signal feature are performed separate from the generating of the stimulation control signals.

6. The method of claim 5, wherein generating the stimulation control signals for use in stimulating the recipient of the hearing device comprises:
executing sound processing operations; and
adjusting one or more of the sound processing operations at least partially based on the environmental classification of the current ambient environment.

7. The method of claim 6, wherein a first environmental classifier is configured to adjust the one or more of the sound processing operations, and a second classifier, which operates independently from the first environmental classifier, is configured to adjust the one or more feature-extraction pre-processing operations.

8. The method of claim 6, wherein a single classifier is configured to both adjust the one or more of the sound processing operations and to adjust the one or more feature-extraction pre-processing operations.

9. The method of claim 4, further comprising:
receiving one or more user inputs; and
adjusting the one or more feature-extraction pre-processing operations at least partially based on the environmental classification of the current ambient environment and at least partially based on the one or more user inputs.

10. The method of claim 1, wherein extracting the at least one signal feature from the one or more input signals based on the environmental classification of the current ambient environment comprises:
extracting at least one measure of fundamental frequency (F0) from the one or more input signals.

11. A method, comprising:
receiving at least one input signal at a hearing device;
determining, from the at least one input signal, an environmental classification of a current ambient environment associated with the at least one input signal;
converting the at least one input signal into stimulation control signals for use in stimulating a recipient of the hearing device;
extracting, using a feature extraction process, one or more signal features from the at least one input signal, wherein one or more parameters of the feature extraction process are controlled based on the environmental classification of the current ambient environment; and
determining at least one feature-based adjustment for incorporation into the stimulation control signals, wherein the at least one feature-based adjustment is based on at least one of the one or more signal features extracted from the at least one input signal.

12. The method of claim 11, wherein determining the at least one feature-based adjustment for incorporation into the stimulation control signals comprises:
executing one or more feature-based adjustment operations to determine the at least one feature-based adjustment for incorporation into the stimulation control signals, wherein one or more parameters of the one or more feature-based adjustment operations are controlled based on the environmental classification of the current ambient environment.

13. The method of claim 11, wherein extracting, using the feature extraction process, the one or more signal features from the at least one input signal comprises:
performing one or more feature-extraction pre-processing operations on the at least one input signal to generate one or more pre-processed signals;
extracting the one or more signal features from the one or more pre-processed signals; and
adjusting one or more parameters of the one or more feature-extraction pre-processing operations based on the environmental classification of the current ambient environment.

14. The method of claim 13, wherein the one or more feature-extraction pre-processing operations and the extracting of the one or more signal features are performed separate from the converting the at least one input signal into the stimulation control signals.

15. The method of claim 13, further comprising:
receiving one or more user inputs; and
adjusting the one or more parameters of a feature-based adjustment one or more feature-extraction pre-processing operations based on the environmental classification of the current ambient environment and based on the one or more user inputs.

16. The method of claim 11, wherein converting the at least one input signal into the stimulation control signals for use in stimulating the recipient of the hearing device comprises:
executing sound processing operations; and
adjusting one or more parameters of one or more of the sound processing operations based on the environmental classification of the current ambient environment.

17. The method of claim 11, wherein extracting, using the feature extraction process, the one or more signal features from the at least one input signal comprises:
extracting at least one measure of fundamental frequency (F0) from the at least one input signal.

18. A method, comprising:
receiving at least one sound signal at an implantable microphone of an implantable medical device;
classifying the at least one sound signal into a selected one of a plurality of categories; and
extracting one or more signal features from the at least one sound signal based on the selected one of the plurality of categories.

19. The method of claim 18, wherein the classifying the at least one sound signal into a selected one of a plurality of categories is based on noise present in the at least one sound signal.

20. The method of claim 18, further comprising:
generating, from the least one sound signal, stimulation control signals for use in stimulating a recipient of the implantable medical device; and
incorporating at least one feature-based adjustment into the stimulation control signals, wherein the at least one feature-based adjustment is based on the at least one signal feature extracted from the at least one sound signal.

21. A medical device, comprising:
one or more microphones configured to receive one or more input signals; and
one or more processors configured to:
determine, based on the one or more input signals, a classification of the one or more input signals, and
perform one or more feature-extraction operations to extract at least one signal feature from the one or more input signals,
wherein the one or more feature-extraction operations are controlled at least partially based on the classification of the one or more input signals.

22. The medical device of claim 21, further comprising:
generating, from the one or more input signals, stimulation control signals for use in stimulating a recipient of the medical device; and
incorporating at least one feature-based adjustment into the stimulation control signals, wherein the at least one feature-based adjustment is based on the at least one signal feature extracted from the one or more input signals.

* * * * *